(12) United States Patent
Nishihara et al.

(10) Patent No.: US 10,499,815 B2
(45) Date of Patent: Dec. 10, 2019

(54) OBJECT INFORMATION ACQUIRING APPARATUS

(71) Applicant: CANON KABUSHIKI KAISHA, Tokyo (JP)

(72) Inventors: Hiroshi Nishihara, Kawasaki (JP); Robert A Kruger, Oriental, NC (US)

(73) Assignee: CANON KABUSHIKI KAISHA, Tokyo (JP)

( * ) Notice: Subject to any disclaimer, the term of this patent is extended or adjusted under 35 U.S.C. 154(b) by 476 days.

(21) Appl. No.: 15/501,682

(22) PCT Filed: Sep. 3, 2015

(86) PCT No.: PCT/JP2015/004473
§ 371 (c)(1),
(2) Date: Feb. 3, 2017

(87) PCT Pub. No.: WO2016/035343
PCT Pub. Date: Mar. 10, 2016

(65) Prior Publication Data
US 2017/0224223 A1      Aug. 10, 2017

Related U.S. Application Data

(60) Provisional application No. 62/046,321, filed on Sep. 5, 2014.

(51) Int. Cl.
*A61B 5/00* (2006.01)
(52) U.S. Cl.
CPC ......... *A61B 5/0095* (2013.01); *A61B 5/4312* (2013.01); *A61B 5/708* (2013.01)

(58) Field of Classification Search
None
See application file for complete search history.

(56) References Cited

U.S. PATENT DOCUMENTS 9,326,688 B2 * 5/2016 Yamamoto ........... A61B 5/0095
9,435,730 B2    9/2016 Nishihara .......... G01N 21/1702
(Continued)

FOREIGN PATENT DOCUMENTS

WO   WO 2013/082586 A   6/2013

OTHER PUBLICATIONS

L.V. Wang et al., "Photoacoustic Tomography: In Vivo Imaging from Organelles to Organs", *Science*, vol. 335, pp. 1458-1462 (Mar. 23, 2012).

(Continued)

*Primary Examiner* — Ankit D Tejani
(74) *Attorney, Agent, or Firm* — Venable LLP

(57) ABSTRACT

Provided is an object information acquiring apparatus including a supporting unit configured to be capable of holding a liquid acoustic matching member, a plurality of receiving elements each supported on the supporting unit to receive an acoustic wave propagated from an object via the acoustic matching member and output an electrical signal, a scanning unit that changes a relative position of each of the receiving elements and the object by moving the supporting unit, a controlling unit that controls a velocity of movement of the supporting unit performed by the scanning unit, and a processing unit that acquires specific information of an inside of the object based on the electrical signal. The scanning unit moves the supporting unit on a path having portions of different curvatures.

16 Claims, 8 Drawing Sheets

(56) References Cited

U.S. PATENT DOCUMENTS

| | | | |
|---|---|---|---|
| 2009/0069653 A1* | 3/2009 | Yoshida | A61B 5/0073 600/323 |
| 2009/0069674 A1* | 3/2009 | Masumura | A61B 5/0073 600/425 |
| 2009/0069676 A1* | 3/2009 | Nishihara | A61B 5/0059 600/437 |
| 2013/0094327 A1 | 4/2013 | Nakabayashi | 367/87 |
| 2013/0165765 A1* | 6/2013 | Nishihara | A61B 6/5247 600/407 |
| 2013/0231549 A1* | 9/2013 | Yamamoto | A61B 5/0095 600/407 |
| 2014/0150182 A1* | 6/2014 | Nishihara | A61B 6/0435 5/601 |
| 2015/0119682 A1* | 4/2015 | Nagae | A61B 5/004 600/407 |
| 2015/0119683 A1* | 4/2015 | Kyono | A61B 5/704 600/407 |
| 2016/0066792 A1 | 3/2016 | Oyama et al. | A61B 5/0095 |
| 2016/0066793 A1 | 3/2016 | Yamamoto et al. | A61B 5/0095 |
| 2016/0069837 A1 | 3/2016 | Nakabayashi et al. | G01N 29/024 |
| 2016/0135688 A1* | 5/2016 | Ebisawa | A61B 5/0095 600/407 |
| 2016/0192843 A1* | 7/2016 | Kruger | A61B 5/0095 600/407 |
| 2016/0213257 A1* | 7/2016 | Nishihara | A61B 5/14551 |
| 2017/0065180 A1 | 3/2017 | Miyasato et al. | 600/407 |
| 2017/0065181 A1 | 3/2017 | Masaki et al. | 600/407 |
| 2017/0303793 A1* | 10/2017 | Fukutani | A61B 5/708 |
| 2017/0325691 A1* | 11/2017 | Nishihara | A61B 5/708 |
| 2017/0325692 A1* | 11/2017 | Nishihara | A61B 8/0825 |
| 2017/0347889 A1* | 12/2017 | Yamamoto | A61B 5/0095 |
| 2018/0103849 A1* | 4/2018 | Iizuka | A61B 5/0073 |
| 2018/0360322 A1* | 12/2018 | Nagae | A61B 5/742 |

OTHER PUBLICATIONS

R.A. Kruger, "Dedicated 3D Photoacoustic Breast Imaging", *Medical Physics*, vol. 40, No. 11, pp. 113301-1-113301-8 (Nov. 2013).

* cited by examiner

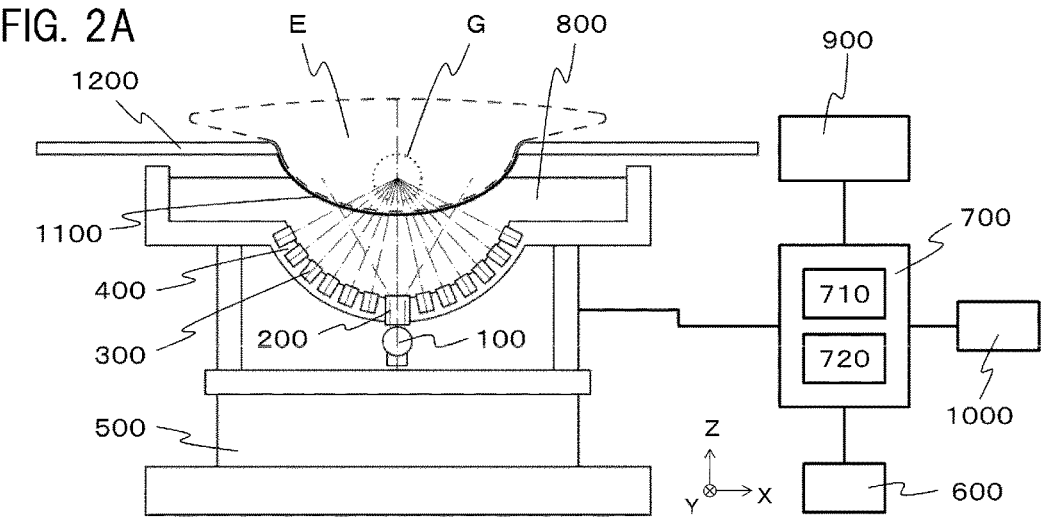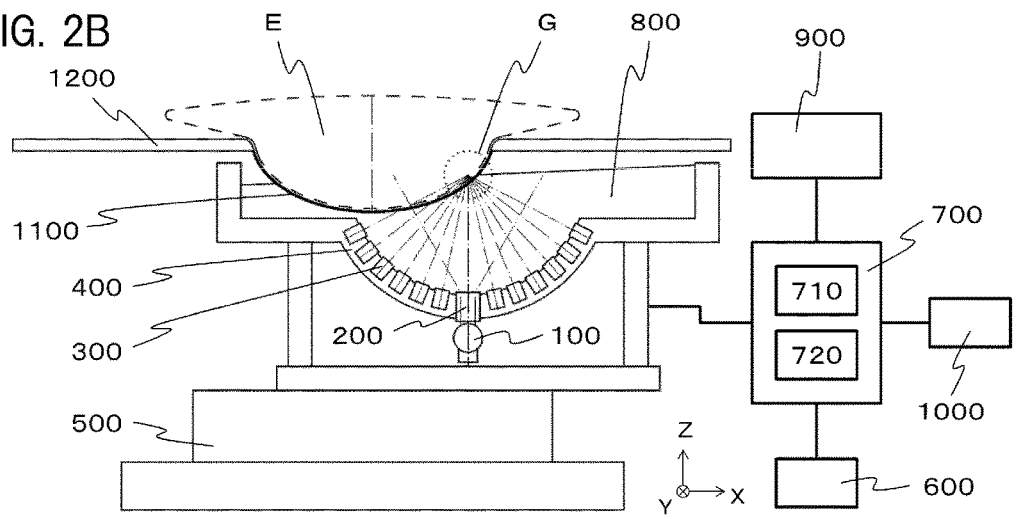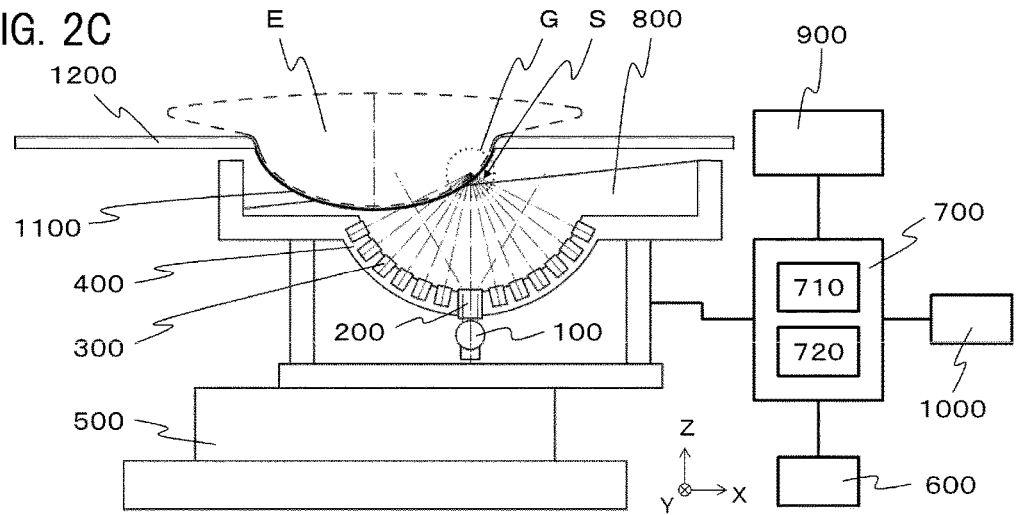

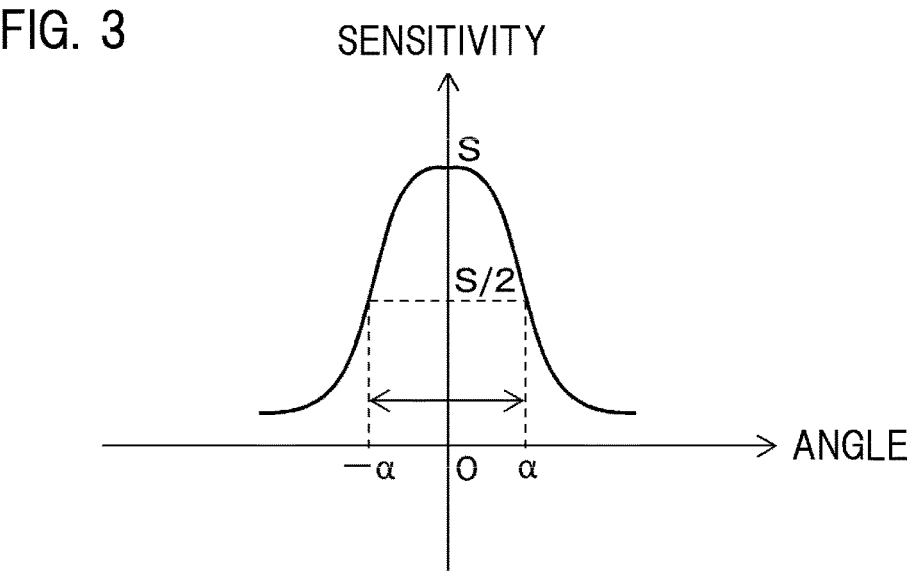

OBJECT INFORMATION ACQUIRING APPARATUS

This application claims the benefit of U.S. Provisional Application No. 62/046,321, filed on Sep. 5, 2014, which is hereby incorporated by reference herein in its entirety.

TECHNICAL FIELD

The present invention relates to an object information acquiring apparatus.

BACKGROUND ART

Researches on an optical imaging apparatus that irradiates an object, such as a biological body, with light from a light source, such as laser, and images information within the object obtained based on incident light have been active in the medical field. Photoacoustic imaging (PAI) is one of such optical imaging techniques. In photoacoustic imaging, an object is irradiated with pulsed light generated from a light source, acoustic waves (typically ultrasound waves) generated from an object tissue that has absorbed energy of the pulsed light propagated/diffused within the object is received, and object information is imaged based on the received signal.

When the object is irradiated with light, an object segment that has absorbed light energy momentarily expands and generates acoustic waves (called photoacoustic waves), due to the difference in absorption rate of light energy between a target segment, such as tumor, and other tissues. In photoacoustic imaging, photoacoustic waves generated by this photoacoustic effect are received utilizing a probe (receiving element).

By performing analytical processing of the received signal mathematically, information within the object, particularly initial sound pressure distribution, light energy absorption density distribution, absorption coefficient distribution, or the like, can be acquired. Such information can also be utilized in quantitative measurement of a particular substance within the object such as, for example, blood oxygen saturation. In recent years, preclinical researches on imaging of a blood vessel image of a small animal using photoacoustic imaging or clinical researches on applying this principle to diagnosis of breast cancer or the like have been active (NPL 1).

NPL 2 describes a testing apparatus that acquires information of an object, using a sensor in which receiving surfaces of a plurality of receiving elements are arranged on the inner surface of a hemispherical supporting unit. Since photoacoustic waves generated in a particular region can be received at a high sensitivity with the sensor, the resolution of object information in the particular region is high.

In the testing apparatus in NPL 2, the inside of the hemispherical supporting unit is filled with an acoustic matching member formed of liquid or gel for propagating photoacoustic waves to an ultrasound probe. It is indicated that information of an object with high resolution is acquired in a wide range by moving the position of the sensor in the horizontal direction with respect to the object immersed in the acoustic matching member.

A container-shaped sensor inside which a liquid acoustic matching member is held can be utilized not only for photoacoustic imaging but also for ultrasound echo diagnosis. In the case of using such a sensor, it is preferable that an acoustic matching member fill the gap between an object and the sensor and the sensor and the object be coupled acoustically.

CITATION LIST

Non Patent Literature

[NPL 1]
"Photoacoustic Tomography: In Vivo Imaging From Organelles to Organs", Lihong V. Wang, Song Hu, Science 335,1458 (2012)

[NPL 2]
"Dedicated 3D Photoacoustic Breast Imaging", Robert A. Kruger, Cherie M. Kuzmiak, Richard B. Lam, Daniel R. Reinecke, Stephen P. Del Rio, and Doreen Steed, Medical Physics 40, 113301 (2013)

SUMMARY OF INVENTION

Technical Problem

However, in the testing apparatus described in NPL 2, there has been room for improvement in terms of clear reception of acoustic waves. Thus, an object of the present invention is to enable clear reception of acoustic waves in an apparatus in which a sensor holding an acoustic matching member is moved to receive acoustic waves from an object.

Solution to Problem

The present invention provides an object information acquiring apparatus comprising:
a supporting unit configured to be capable of holding liquid acoustic matching member;
a plurality of receiving elements each supported on the supporting unit to receive an acoustic wave propagated from an object via the acoustic matching member and output an electrical signal;
a scanning unit that changes a relative position of the plurality of receiving elements and the object by moving the supporting unit;
a controlling unit that controls a velocity of movement of the supporting unit performed by the scanning unit; and
a processing unit that acquires specific information of an inside of the object based on the electrical signal,
wherein the scanning unit moves the supporting unit on a path having portions of different curvatures, and
the controlling unit controls the movement velocity in accordance with a magnitude of the curvature.

The present invention also provides an object information acquiring apparatus comprising:
a supporting unit configured to be capable of holding a liquid acoustic matching member;
a plurality of ultrasound wave receiving elements each supported on the supporting unit to receive an acoustic wave propagated from an object via the acoustic matching member;
a scanning unit that changes a relative position of the supporting unit and the object by moving the supporting unit;
and a controlling unit that controls a velocity of movement of the supporting unit performed by the scanning unit,
wherein the scanning unit moves the supporting unit on a path including a first portion having a first curvature radius and a second portion having a second curvature radius smaller than the first curvature radius, and the controlling unit controls the movement velocity of the supporting unit such that the velocity of the supporting unit when moving in the second portion becomes lower than the velocity of the supporting unit when moving in the first portion.

Advantageous Effects of Invention

With the present invention, clear reception of acoustic waves is possible in an apparatus in which a sensor holding an acoustic matching member is moved to receive acoustic waves from an object.

Further features of the present invention will become apparent from the following description of exemplary embodiments with reference to the attached drawings.

BRIEF DESCRIPTION OF DRAWINGS

FIGS. 2A to 2C are diagrams representing a modified example of the configuration and behavior of an apparatus.

FIG. 3 is a diagram representing the sensitivity characteristics of an acoustic wave receiving element.

DESCRIPTION OF EMBODIMENTS

Figure 1A:
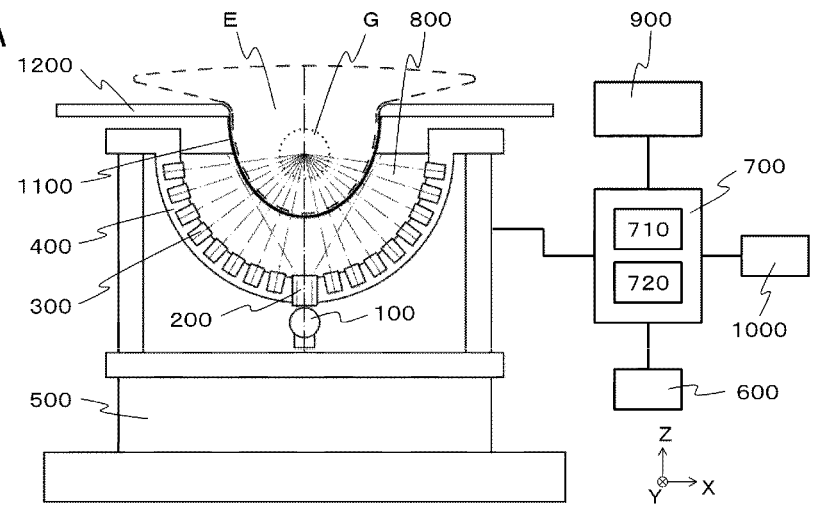
FIGS. 1A to 1C are diagrams representing the configuration and behavior of an apparatus.

A preferred embodiment of the present invention will be described below with reference to the drawings. Note that the dimension, material, and shape of components described below, the relative arrangement thereof, and the like should be changed appropriately depending on the configuration or various conditions of an apparatus to which the invention is applied, and it is not the intention to limit the scope of the invention to the description below.

The present invention relates to a technique in which acoustic waves that propagate from an object are detected and specific information of the inside of the object is generated and acquired. Thus, the present invention can be understood as an object information acquiring apparatus, a method of controlling the same, an object information acquiring method, or a signal processing method. The present invention can also be understood as a program that causes an information processing apparatus including a hardware resource, such as a CPU, to execute these methods or a storage medium that stores the program. The present invention can also be understood as an acoustic wave measuring apparatus or a method of controlling the same.

The present invention can be applied to an object information acquiring apparatus utilizing a photoacoustic tomography technique that irradiates an object with light (electromagnetic waves) and receives (detects) acoustic waves generated at and propagated from a specific position within the object or on the object surface according to a photoacoustic effect. Such an apparatus can also be called a photoacoustic imaging apparatus, a photoacoustic image-forming apparatus, or simply a photoacoustic apparatus, since specific information of the inside of an object can be obtained in the form of image data, characteristic distribution information, or the like based on photoacoustic measurement. Alternatively, an apparatus of the present invention tests the inside of an object, and therefore may be called a testing apparatus.

Specific information in a photoacoustic apparatus is generation source distribution of acoustic waves caused by light irradiation, initial sound pressure distribution within an object, light energy absorption density distribution or absorption coefficient distribution derived from initial sound pressure distribution, concentration distribution of a substance forming a tissue, or the like. The concentration of a substance is oxygen saturation, oxyhemoglobin concentration, deoxyhemoglobin concentration, total hemoglobin concentration, or the like. Total hemoglobin concentration is the sum of oxyhemoglobin concentration and deoxyhemoglobin concentration. Distribution or the like of fat, collagen, or moisture is also included. Specific information may be obtained not as numerical data but as distribution information of each position within an object. That is, distribution information of absorption coefficient distribution, oxygen saturation distribution, or the like may be object information.

The present invention can be applied to an apparatus utilizing an ultrasound echo technique in which ultrasound waves are transmitted to an object, reflected waves (echo waves) reflected inside the object are received, and object information is acquired as image data. In the case of the apparatus utilizing the ultrasound echo technique, the acquired object information is information reflecting the difference in acoustic impedance of tissues inside the object.

Acoustic waves referred to in the present invention are typically ultrasound waves and include elastic waves called sound waves or acoustic waves. Acoustic waves generated by a photoacoustic effect are called photoacoustic waves or light-induced ultrasound waves. An electric signal converted from acoustic waves by a probe is also called an acoustic signal, and an acoustic signal originating from photoacoustic waves is particularly called a photoacoustic signal.

As an object in the present invention, a breast of a biological body can be expected. Note that an object is not limited as such, and it is possible to test other segments of a biological body or a non-biological material. Thus, the present invention can also be understood as an object information acquiring apparatus or a method of controlling the same.

According to a study by the inventors, inertia force acts on an acoustic matching member and the liquid surface oscillates, when the position of a sensor filled with the acoustic matching member is moved in the horizontal direction in an object information acquiring apparatus according to NPL 2. When the oscillation of the liquid surface increases, there are cases where an air layer not filled with the acoustic matching member is formed between the object and the sensor, such that a receiving element cannot receive acoustic waves. Thus, in the embodiment below, an apparatus configuration and behavior to reduce the influence of such oscillation of the liquid surface will be described.

(Outline of the Invention)

An object information acquiring apparatus of the present invention includes a plurality of acoustic wave receiving elements and a supporting unit that supports an acoustic matching member to propagate acoustic waves generated from an object to the acoustic wave receiving element, so that acoustic waves generated in a specific region can be received at a high sensitivity. In this embodiment, the specific region is called a high-sensitivity region.

The object information acquiring apparatus of the present invention includes a scanning unit with which the position of the supporting unit is moved with respect to an object in the horizontal direction on a curved path having portions of different curvatures, so that the object can be tested at a high sensitivity in a wide range. Further, the object information acquiring apparatus of the present invention includes a controlling unit that controls the scanning unit to set the velocity of moving the supporting unit in accordance with the curvature of the curved path.

The object information acquiring apparatus with the configuration described above controls the velocity of movement to decelerate in the case where the curvature of the path increases, upon moving the position of the supporting unit filled with the acoustic matching member in the horizontal direction. Accordingly, the inertia force that acts on the acoustic matching member decreases, and the oscillation of the liquid surface also decreases. With such control, the oscillation of the liquid surface of the acoustic matching member due to the inertia force can be reduced to within permissible range. As a result, the acoustic matching member fills the gap between the object and the acoustic wave receiving element. Therefore, acoustic waves emitted from the object to which the acoustic wave receiving element is acoustically coupled can be received clearly.

The object information acquiring apparatus with the configuration described above controls the velocity of movement to accelerate in the case where the curvature of the path in which the position of the supporting unit filled with the acoustic matching member is moved in the horizontal direction decreases. When the oscillation of the liquid surface of the acoustic matching member due to the inertia force is reduced to within permissible range by such control, the acoustic matching member fills the gap between the object and the acoustic wave receiving element. As a result, it is possible to clearly receive acoustic waves emitted from the object to which the acoustic wave receiving element is acoustically coupled. Further, a state where acoustic waves emitted from the object to which the acoustic wave receiving element is acoustically coupled can be clearly received is maintained, and the measurement time can be shortened.

The movement velocity (velocity of changing the relative position of the receiving element and the object) in the present application is the velocity in the tangential direction on the path having curvature. The velocity in the tangential direction means the distance of movement per unit time that is represented in units of mm/sec, for example, and does not mean the so-called angular velocity (rad/sec).

(Embodiment 1)

Figure 1B:
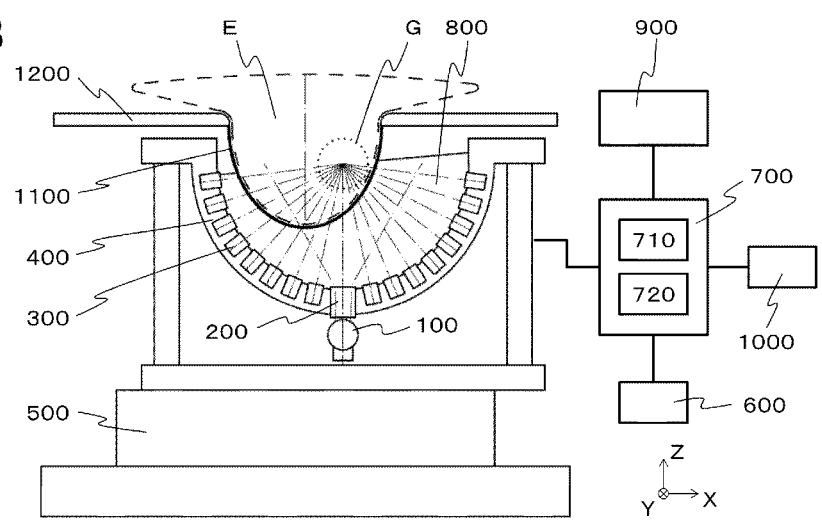
Figure 1C:
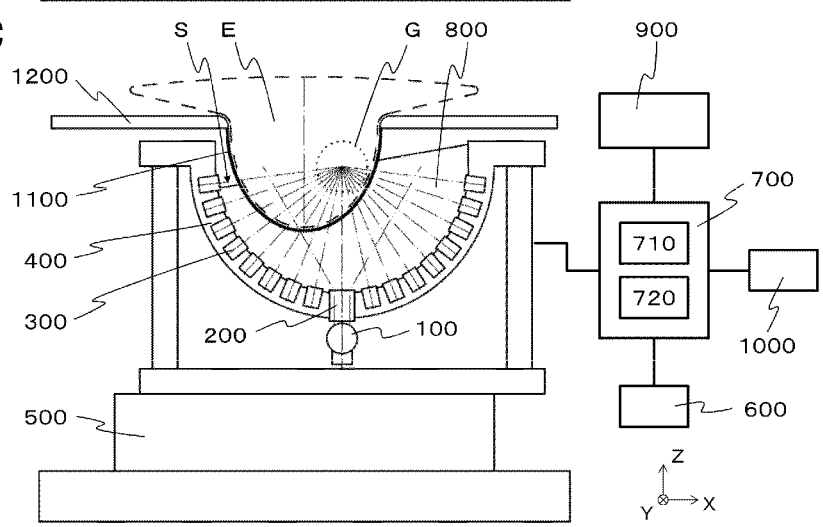

FIG. 1 (FIGS. 1A to 1C) and FIG. 2 (FIGS. 2A to 2C) are schematic diagrams showing the configuration and behavior of an object information acquiring apparatus according to this embodiment. The object information acquiring apparatus acquires specific information (object information) of an object E based on a received signal of acoustic waves generated by a photoacoustic effect.

<Basic Configuration>

The object information acquiring apparatus in this embodiment includes a light source 100, an optical system 200, a plurality of acoustic wave receiving elements 300, a supporting unit 400, a scanner 500, a shape information acquiring unit 600, a computer 700, a display 900, an inputting unit 1000, and a shape holding unit 1100.

(Object)

The object E is a target of measurement. Specific examples include a biological body, such as a breast, and a phantom simulating the acoustic characteristics and optical characteristics of a biological body that is used for adjustment or correction of an apparatus. The acoustic characteristics are specifically propagating velocity and decay rate of acoustic waves. The optical characteristics are specifically absorption coefficient and scattering coefficient of light. Inside or at the surface of the object, a light absorber with a large light absorption coefficient exists. In a biological body, hemoglobin, water, melanin, collagen, fat, or the like is the light absorber. In a phantom, a substance simulating the optical characteristics is encapsulated inside as the light absorber. For the sake of convenience, the object E is shown by a broken line in FIG. 1 and FIG. 2.

(Light Source)

The light source 100 generates pulsed light. As a light source, laser is desirable in order to obtain a large input, but a light-emitting diode or the like is acceptable. In order to generate photoacoustic waves effectively, light irradiation needs to be performed in a sufficiently short period of time in accordance with the thermal characteristics of an object. In the case where the object is a biological body, the pulse width of pulsed light generated from the light source 100 is desirably less than or equal to several tens of nanoseconds. The wavelength of pulsed light is in the near-infrared region that is called the biological window, and approximately 700 nm to 1200 nm is desirable. Light in this region can reach into a relatively deep part of a biological body, and information of the deep part can be obtained. When measurement is limited to the surface part of a biological body, visible light of approximately 500 to 700 nm up to the near-infrared region may be used. Further, the wavelength of pulsed light is desirably high in absorption coefficient with respect to the target of observation. The light source 100, such as laser, does not necessarily need to move in synchronization with the supporting unit 400 described later. The light source 100 can be arranged in a position to not coordinate with the movement of the supporting unit 400, such that light from the light source is guided into the supporting unit by an optical waveguide, such as optical fiber.

(Optical System)

The optical system 200 guides pulsed light generated at the light source 100 to the object E. Specifically, it is optical equipment such as a lens, mirror, prism, optical fiber, or diffuser or a combination thereof. Upon guiding light, it is preferable to change the shape or density of light for a desired light distribution of irradiation light using such optical equipment. In this embodiment, the optical system 200 is configured to illuminate a region at the center of curvature of a hemisphere.

For the intensity of light with which a biological tissue is permitted to be irradiated, the maximum permissible exposure (MPE) is specified by safety standards. Examples of the safety standards include "IEC 60825-1: Safety of laser products." There are safety standards such as "JISC 6802: Safety Standards for Laser Products," "FDA: 21CFR Part 1040.10," and "ANSI Z136.1: Laser Safety Standards." The maximum permissible exposure specifies the intensity of light with which irradiation can be performed per unit area. Therefore, by irradiating a large area of the surface of the object E collectively with light, a large amount of light can be guided to the object E. As a result, photoacoustic waves can be received at a high SN ratio. Therefore, it is preferable to increase the area to a certain extent, as shown by a double-dot-dashed line in FIG. 1 and FIG. 2, than to focus light with a lens.

(Acoustic Wave Receiving Element)

The acoustic wave receiving element 300 is an element with which photoacoustic waves are received and converted to an electrical signal and is also simply called a receiving element. It is desirable that the receiving sensitivity be high and the frequency band be wide with respect to photoacoustic waves from the object E.

For the material of the acoustic wave receiving element 300, a piezo-ceramic material as typified by lead zirconate titanate (PZT), a piezoelectric polymer membrane material as typified by polyvinylidene fluoride (PVDF), or the like can be used. A member not of a piezoelectric material such as a capacitive element, such as a capacitive micro-machined ultrasonic transducer (cMUT), or an acoustic wave receiving element using a Fabry-Perot interferometer may be used.

FIG. 3 shows one example of the receiving sensitivity characteristics of the acoustic wave receiving element 300. The "angle" shown by the abscissa in FIG. 3 is the incident angle formed by the normal direction of the receiving surface of the acoustic wave receiving element 300 and the incident direction of photoacoustic waves. The ordinate shows the relative value of the receiving sensitivity at each incident angle. In FIG. 3, the receiving sensitivity in the case where acoustic waves are incident from the normal direction of the receiving surface is the highest. That is, when the incident angle equals zero, the sensitivity equals S (maximum value). As the incident angle increases, the receiving sensitivity decreases. The acoustic wave receiving element 300 according to this embodiment has a circular and flat-shaped receiving surface.

The incident angle when the receiving sensitivity becomes half of the maximum value (S/2) is α. In this embodiment, a region in which photoacoustic waves are incident upon the receiving surface of the acoustic wave receiving element 300 at the incident angle α or less is a receiving region in which the element is capable of reception at a high sensitivity. Note that the receiving region is not limited to such half width and suffices to be specified in accordance with the element characteristics, the accuracy desired for measurement, or the like. In FIG. 1 and FIG. 2, the direction in which the receiving sensitivity of acoustic wave receiving element 300 is highest is shown by a dashed-dotted line.

As the acoustic wave receiving element 300, an element capable of transmitting and receiving ultrasound waves may be provided. In the case where an element capable of transmitting ultrasound waves and receiving reflected waves is used, not only photoacoustic measurement but also ultrasound echo measurement is possible. In this case, the receiving element also serves as an acoustic wave transmitting unit. In order to perform ultrasound echo measurement, an element dedicated to ultrasound wave transmission may be provided. In this case, the element dedicated to transmission is the acoustic wave transmitting unit.

(Supporting Unit)

The supporting unit 400 is an approximately hemispherical container. The plurality of acoustic wave receiving elements 300 are installed at the surface on the inside of the hemisphere, and the optical system 200 is installed at the bottom part (pole) of the hemisphere. The inside of the hemisphere is filled with an acoustic matching member 800 described later. The supporting unit 400 is preferably configured using a metal material with high mechanical strength in order to support these members.

The receiving directions of the plurality of acoustic wave receiving elements 300 provided to the supporting unit 400 are respectively toward the center of curvature of the hemisphere. The receiving directions are shown by dashed-dotted lines that converge in a region in a part of the object E. FIG. 1 and FIG. 2 are sectional views when cut along the central axis of the hemispherical supporting unit 400.

In this manner, the respective elements of the plurality of acoustic wave receiving elements 300 are arranged on the supporting unit 400 such that photoacoustic waves generated in a specific region can be received at a high sensitivity. In this embodiment, the specific region is called a high-sensitivity region.

In the case of such arrangement of the plurality of acoustic wave receiving elements 300, object information obtained using a received signal with a method described later is high in resolution at the center of curvature of the hemisphere and decreases in resolution away from the center. The high-sensitivity region in this embodiment refers to a region from a point where the resolution is highest up to where the resolution is half the highest resolution. A region G encompassed by a dotted line in FIG. 1 and FIG. 2 corresponds to this.

The supporting unit 400 in FIG. 1 is suitable for a wide-field measurement of a breast hanging in prone position. The supporting unit 400 in FIG. 2 is suitable for measurement of the deep part of a breast, since the breast can be pressed from one side and made thin, although the view angle of measurement becomes narrower than in the object information acquiring apparatus in FIG. 1.

As long as a desired high-sensitivity region can be formed, the directions of the highest sensitivity of the respective acoustic wave receiving elements do not necessarily need to intersect with each other. It suffices that the direction of the highest receiving sensitivity of at least part of the plurality of acoustic wave receiving elements 300 supported by the supporting unit 400 be toward a specific region, so that photoacoustic waves generated in the specific region can be received at a high sensitivity. That is, it suffices that at least part of the plurality of acoustic wave receiving elements 300 be arranged on the supporting unit 400, so that photoacoustic waves generated in the high-sensitivity region can be received at a high sensitivity.

The shape of the supporting unit 400 is not limited to a hemisphere. A spherical crown shape, a shape of a portion cut out from an ellipsoid, a shape in which a plurality of flat surfaces or curved surface are combined, or the like can also be used. A shape having a depressed portion capable of housing the acoustic matching member can also be used. A shape that can support a plurality of acoustic detecting elements is desirable, so that receiving directions of at least part of the plurality of acoustic detecting elements converge.

In an apparatus that moves the supporting unit 400 in the horizontal direction to follow a circular or spiral path with a scanner (scanning unit) described later, it is advisable that the supporting unit 400 be in a rotationally symmetrical shape about the central axis of the hemisphere. Since inertia force acts on the acoustic matching member in the normal direction of the circular or spiral path to tilt the liquid surface, a change of the liquid surface can be moderated by making the supporting unit 400 in the rotationally symmetrical shape relating to the circular or spiral path.

(Scanner)

The scanner 500 is an apparatus that changes the relative position of the supporting unit 400 with respect to the object E by moving the position of the supporting unit 400 in the X- and Y-directions in FIG. 1 and FIG. 2. Therefore, the scanner 500 includes a guide mechanism for the X- and Y-directions, a drive mechanism for the X- and Y-directions, and a position sensor that detects the position of the supporting unit 400 in the X- and Y-directions that are not shown. Since the supporting unit 400 is stacked on the scanner 500 as shown in FIG. 1 and FIG. 2, it is preferable to use a linear guide capable of withstanding a large load as the guide mechanism. As the drive mechanism, a lead screw mechanism, a link mechanism, a gear mechanism, a hydraulic mechanism, or the like can be used. For the drive force, a motor or the like can be used. As the position sensor, a potentiometer or the like using an encoder, variable resistor, or the like can be used.

It is not limited to those listed herein, and anything suffices as long as the configuration enables movement of the supporting unit 400 with respect to the object E. The supporting unit 400 can be moved by a movable mechanism, in addition to the drive mechanism in the X- and Y-directions, in the Z-direction orthogonal to the axial directions thereof.

It is also possible to move the supporting unit 400 to follow a path including, for example, a first portion having a first curvature radius and a second portion having a second curvature radius smaller than the first curvature radius. At that time, the controlling unit controls the movement velocity of the supporting unit such that the velocity of the supporting unit when moving in the second portion becomes lower than the velocity of the supporting unit when moving in the first portion.

(Shape Information Acquiring Unit)

The shape information acquiring unit 600 is an apparatus that acquires shape information representing the external shape of the object E. The shape information acquiring unit 600 can include an imaging apparatus that can image the object E, such as, for example, a camera or a transducer array that transmits and receives acoustic waves. As the transducer, a transducer provided separately from the plurality of the acoustic wave receiving elements 300 or at least one element of the plurality of acoustic wave receiving elements 300, or the like can be employed. Such a transducer can transmit acoustic waves and receive reflected waves of the acoustic waves.

It may be such that an arithmetic unit 710 as a taken image processing unit acquires a taken image based on a received signal output from such an imaging apparatus, and shape information of the object E is acquired by image processing based on the taken image. The arithmetic unit 710 may acquire shape information of the object E using a three-dimensional measuring technique, such as the stereo method, based on taken images taken from a plurality of directions. A user may look at a taken image displayed in the display 900 and input shape information of the object E with the inputting unit 1000. In this case, the imaging apparatus and the taken image processing unit can be collectively called the shape information acquiring unit 600.

As the shape information acquiring unit 600, a contact probe may be used. In this case, the arithmetic unit can acquire shape information of the surface of the object E based on data output from the contact probe.

The shape of the shape holding unit 1100 may be acquired as shape information of the object E. In this case, it may be such that the shape information acquiring unit 600 acquires shape information of the shape holding unit 1100 with the method described above, and the shape information of the shape holding unit 1100 is acquired as information of the object E. It may be such that shape information of the shape holding unit 1100 is stored in a storage unit 720 in advance, and the shape information acquiring unit 600 acquires the shape information of the shape holding unit 1100 by reading the information from the storage unit 720. The arithmetic unit 710 may also serve as the shape information acquiring unit 600.

Further, in the case of using a plurality of shape holding units, it is preferable that shape information of each shape holding unit be stored in the storage unit 720. The shape information of the shape holding unit used by the shape information acquiring unit 600 may be read from the storage unit 720, by the shape holding unit to be used being identified by the object information acquiring apparatus or being designated by a user with the inputting unit 1000. That is, the shape information acquiring unit 600 may select shape information of one shape holding unit from shape information of the plurality of shape holding units and acquire the selected shape information as shape information of the object.

The shape information acquiring unit 600 may be provided separately from the object information acquiring apparatus.

(Computer)

The computer 700 has the arithmetic unit 710 and the storage unit 720.

The arithmetic unit 710 is typically configured of an element, such as a CPU, GPU, A/D converter, or amplifier, or a circuit, such as an FPGA or ASIC. The arithmetic unit may be not configured of one element or circuit but be configured of a plurality of elements or circuits. Each processing performed by the computer 700 may be executed by any one of the elements or circuits.

The storage unit 720 is typically configured of a storage medium, such as a ROM, RAM, or hard disk. The storage unit may be not configured of one storage medium but be configured of a plurality of storage media.

Figure 4:
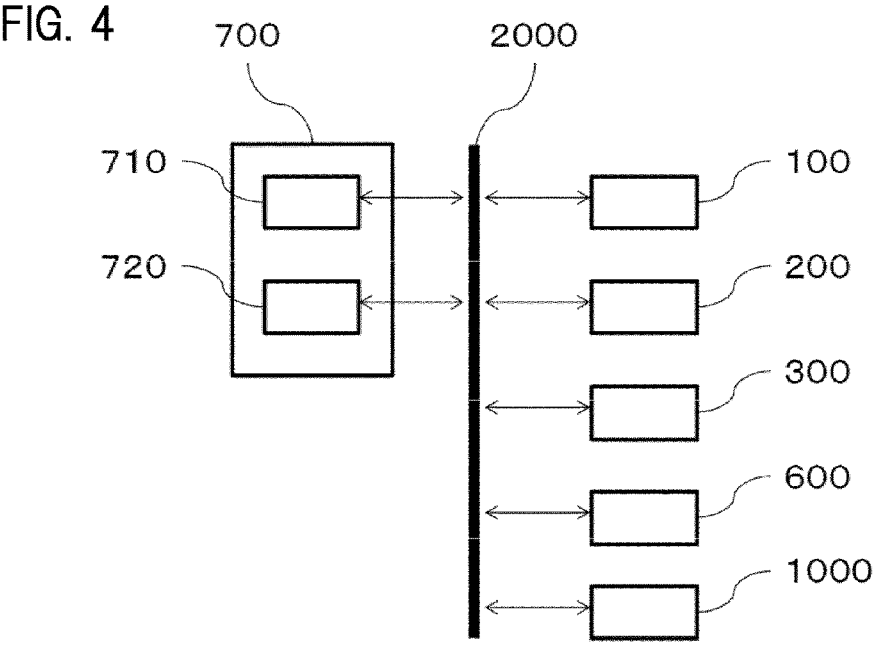
FIG. 4 is a diagram showing the connection of a computer and peripheral equipment thereof.

The arithmetic unit 710 carries out signal processing with respect to an electrical signal output from the plurality of acoustic wave receiving elements 300. The arithmetic unit 710 as the controlling unit controls the behavior of each configuration forming the object information acquiring apparatus via a bus 2000, as shown in FIG. 4.

The computer 700 is preferably configured to allow pipeline processing of a plurality of signals simultaneously. Accordingly, time until the acquisition of object information can be shortened.

Each processing performed by the computer 700 can be saved in the storage unit 720 as a program to be executed by the arithmetic unit 710. Note that the storage unit 720 in which the program is saved is a non-transitory recording medium.

(Acoustic Matching Member)

The acoustic matching member 800 fills the space between the object E and the acoustic wave receiving element 300 and acoustically couples the object E and the acoustic wave receiving element 300. Therefore, it is preferable to arrange the acoustic matching member 800 between the acoustic wave receiving element 300 and the shape holding unit 1100 and between the shape holding unit 1100 and the object E. Different acoustic matching members 800 may be arranged respectively between the acoustic wave receiving element 300 and the shape holding unit 1100 and between the shape holding unit 1100 and the object E.

The acoustic matching member 800 is preferably a material that is close in acoustic impedance to the object E and the acoustic wave receiving element 300. Further, the acoustic matching member 800 is preferably a material having an intermediate acoustic impedance between the object E and the acoustic wave receiving element 300. The acoustic matching member 800 is preferably a material that allows pulsed light generated at the light source 100 to pass through. The acoustic matching member 800 is preferably liquid. Specifically, as the acoustic matching member 800, gel or the like can be used, aside from liquid such as water or castor oil.

(Display)

The display 900 (displaying unit) displays object information output from the computer 700 with a distribution image or numerical data of a specific region of concern. The display may be any type of display, such as a liquid crystal display, plasma display, organic EL display, or FED. The display 900 may be provided separately from the object information acquiring apparatus of the present invention.

(Inputting Unit)

The inputting unit 1000 is a user interface for a user to input and designate desired information in the computer 700. As the inputting unit 1000, a keyboard, mouse, touch panel, dial, button, or the like can be utilized. In the case of employing a touch panel as the inputting unit 1000, the display 900 may be a touch panel that also serves as the inputting unit 1000.

(Shape Holding Unit)

The shape holding unit 1100 is a member for holding the shape of the object E to be constant. The shape holding unit 1100 is attached to an attaching unit 1200. In order to change the held shape of the object E or deal with individual difference in the size of the object E, a configuration in which a plurality of shape holding units with different shapes or sizes are replaceable is preferable.

In the case where the object E is a breast, the shape holding unit 1100 is preferably in a spherical crown shape or a cup shape in order to reduce deformation of the breast shape. The shape of the shape holding unit 1100 can be appropriately designed in accordance with the volume of the object or the desired shape after being held.

In the case of irradiating the object E with light via the shape holding unit 1100, the shape holding unit 1100 preferably causes irradiation light to pass through. Therefore, as the material of the shape holding unit 1100, polymethylpentene, polyethylene terephthalate, or the like is suitable.

As another material of the shape holding unit 1100, a material having flexibility, such as rubber, capable of deformation to adapt to the shape of the object E can be used. A material having flexibility is advantageous in that a wrinkle is less likely to be formed at the time of holding the object E. It is preferable to use a member with a high transmittance (preferably greater than or equal to 90%) for light of the light source 100. Specifically, silicone rubber, urethane rubber, styrene-based elastomer, olefin-based elastomer, acryl-based elastomer, or the like is suitable.

<Behavior of Object Information Acquiring Apparatus>

Next, the behavior of the object information acquiring apparatus will be described. The behavior in this embodiment is a behavior such that the acoustic wave receiving element 300 can clearly receive acoustic waves emitted from the object E even if the position of the supporting unit 400 is moved in the horizontal direction, in a state where the acoustic matching member 800 has filled the gap between the object E and the acoustic wave receiving element 300.

Figure 5:
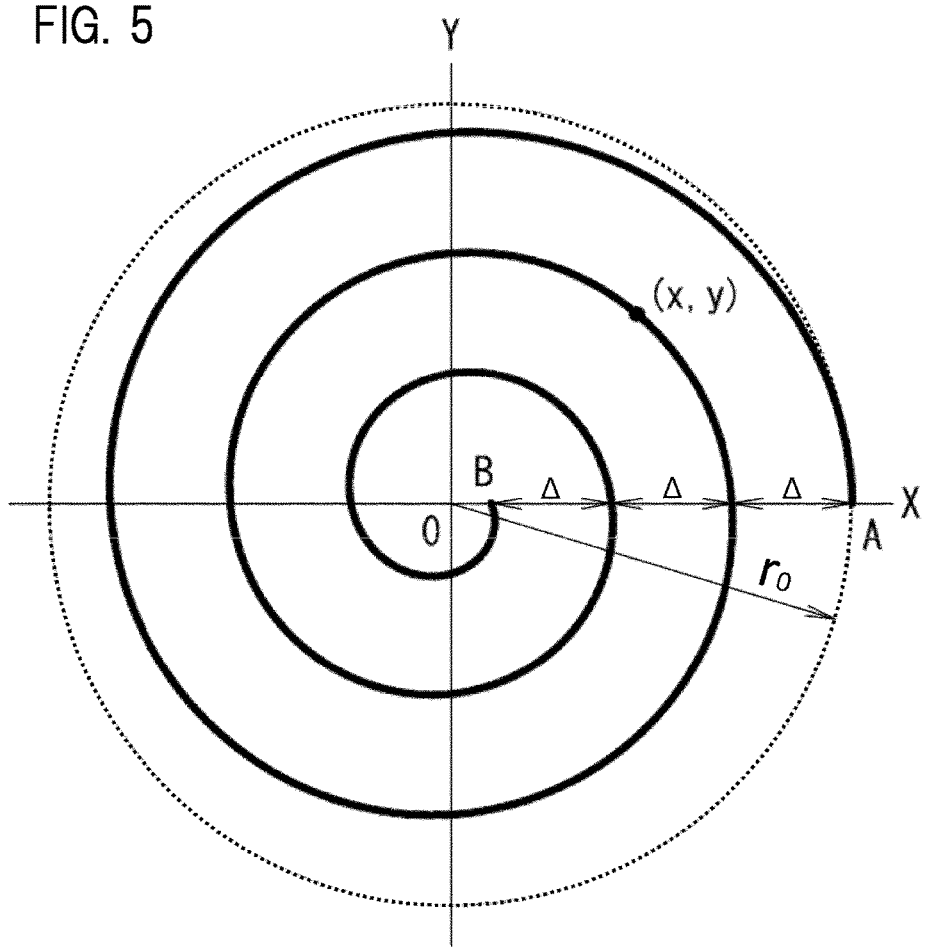
FIG. 5 is a diagram for illustrating the movement region of a supporting unit.

FIG. 5 shows one example of the movement region in the X- and Y-directions of the supporting unit 400 adapted to the shape holding unit 1100. In this example, a spiral path starts from a point A at a radius $r_0$ and reaches a point B after three rounds while decreasing by $\Delta$ in radius in every round. The spiral path shown by a bold line shows the path of the center point of the supporting unit 400, for example. The spiral path is represented by the following formula (1).

[Math. 1]

$$x = r \cdot \cos\theta \quad (1)$$
$$y = r \cdot \sin\theta$$
$$r = r_0 - \frac{\Delta}{2\pi} \cdot \theta$$
$$0 \leq \theta \leq 3\pi$$

As can be seen from FIG. 5 and formula (1), the curvature differs depending on the position, since a curvature radius r of the path of the supporting unit 400 changes bit by bit. That is, the supporting unit 400 receives acoustic waves propagating from the object, while moving on the curved path including portions of different curvatures. The curved path may be an approximately arc path described earlier in which micro linear paths are connected. The supporting unit may receive acoustic waves while moving continuously or may receive acoustic waves in a stopping part while repeating stopping and moving. At this time, the supporting unit moves while changing a velocity v (mm/sec) linearly. An electrical signal output from the receiving element is subjected to processing based on an image reconstruction algorithm by a computer and becomes specific information of the inside of the object.

FIG. 1A and FIG. 2A show states in which the supporting unit 400 filled with the acoustic matching member 800 is stopped, and the liquid surface of the acoustic matching member 800 is horizontal.

FIG. 1B and FIG. 2B show states after the supporting unit 400 filled with the acoustic matching member 800 has started to move on the curved path after moving to the starting position A in FIG. 5. In FIG. 1B and FIG. 2B, inertia force acts on the acoustic matching member 800 to tilt the liquid surface from being horizontal, due to the movement of the supporting unit 400. However, at this stage, the gap between all of the acoustic wave receiving elements 300 and the shape holding unit 1100 holding the object E is filled by the acoustic matching member 800. Therefore, acoustic coupling of the two is held.

FIG. 1C and FIG. 2C show states where a larger inertia force than in FIG. 1 and FIG. 2B has acted on the acoustic matching member 800. Therefore, in FIG. 1C and FIG. 2C, the liquid surface of the acoustic matching member 800 is more tilted than in the states in FIG. 1B and FIG. 2B. As a result, space (air layer) that is not filled with the acoustic matching member 800 is formed in the gap (shown by an arrow S) between part of the acoustic wave receiving elements 300 and the shape holding unit 1100 holding the object E. Thus, part of the acoustic wave receiving elements 300 are not acoustically coupled with the object E and therefore cannot receive photoacoustic waves.

In this embodiment, a state where the normal line of the receiving surface of the acoustic wave receiving element 300 intersects with the space (air layer) not filled with the acoustic matching member 800 is assumed as a state where the object E and the acoustic wave receiving element 300 are not acoustically coupled. In the example in FIG. 1C, the receiving surfaces of part of the acoustic wave receiving elements 300 are exposed to the space (air layer) not filled with the acoustic matching member 800. In the example in FIG. 2C, the receiving surfaces of all of the acoustic wave receiving elements 300 are in contact with the acoustic matching member 800, but the space (air layer) not filled with the acoustic matching member 800 is formed between the direction in which the acoustic wave receiving element 300 is capable of reception at a high sensitivity and the object E.

An inertia force F acting on the acoustic matching member 800 is represented by the following formula (2), where the mass of the acoustic matching member 800 on which the inertia force acts is m and the movement velocity is v.

[Math. 2]

$$F = \frac{mv^2}{r} \quad (2)$$

Assuming the maximum inertia force in the case where the object E and the acoustic wave receiving element 300 are acoustically coupled as $F_{max}$, the gap between the object E and the acoustic wave receiving element 300 can be filled with the acoustic matching member 800 by controlling the movement velocity v (mm/sec) to satisfy the condition of formula (3). Accordingly, the object E and the acoustic wave receiving element 300 can be acoustically coupled.

[Math. 3]

$$F_{max} \geqq \frac{mv^2}{r} \quad (3)$$

<Velocity Controlling Method>

Figure 8:
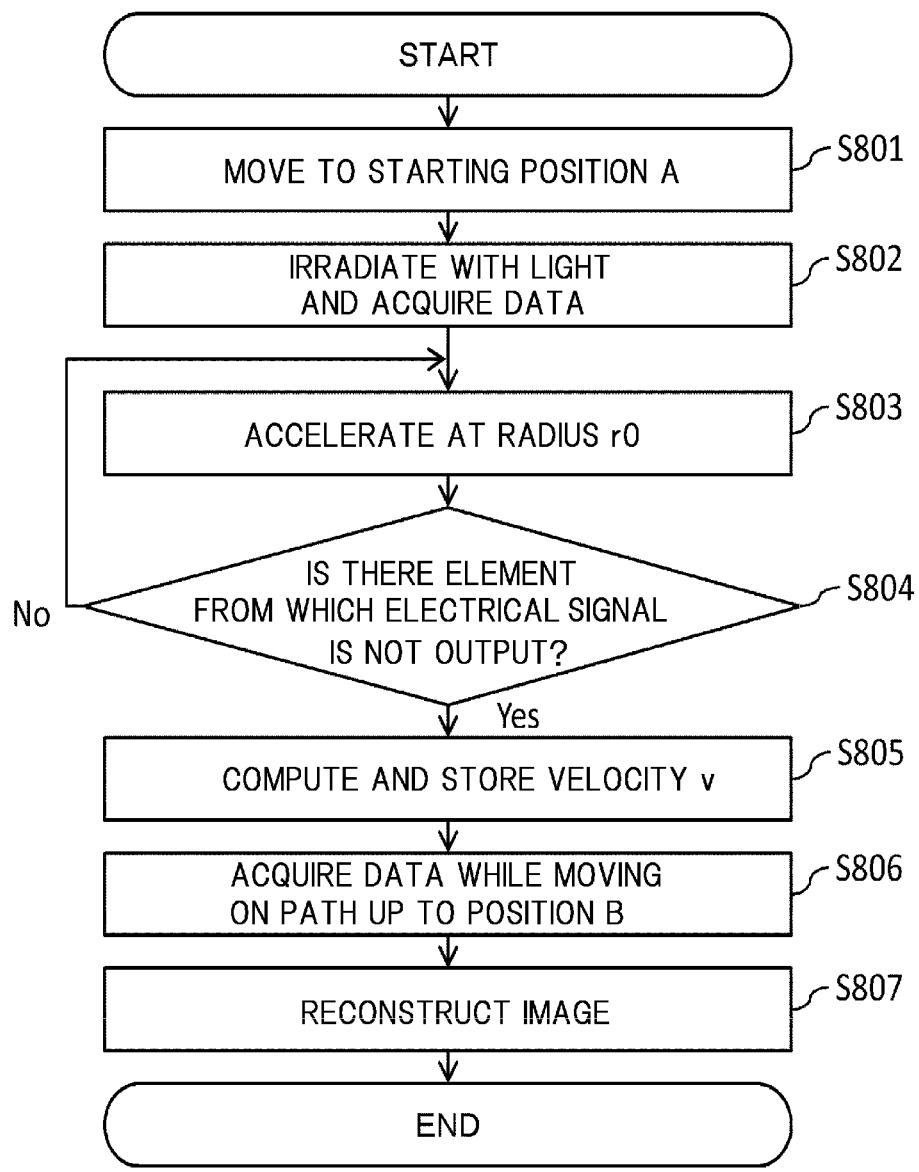
FIG. 8 is a flowchart showing a velocity controlling method.

Next, a specific method for controlling the movement velocity v (mm/sec) will be described. A flowchart shown in FIG. 8 will be referenced as necessary. In this embodiment, the object E shown in FIG. 1 and FIG. 2 is expected to be a breast, and a holder that is in the shape of a partial sphere is used for the shape holding unit 1100.

First, the object E is inserted to the shape holding unit 1100, and the acoustic matching member 800 fills the gap between the supporting unit 400 and the shape holding unit 1100 and the gap between the shape holding unit 1100 and the object E. An operator (such as a technician or doctor) of the object information acquiring apparatus inputs the turning radius $r_0$ with the inputting unit 1000, in order to move the supporting unit 400 in a circular path. The flow starts in this state. The turning radius is at $r_0$ that is the maximum value shown in FIG. 5, to find the maximum value of the movement velocity v (mm/sec) to satisfy the condition of formula (3).

With the scanner 500, the supporting unit 400 is moved and stopped at the position A where measurement is to be started with the turning radius $r_0$ (step S801). At this time, the supporting unit 400 filled with the acoustic matching member 800 is stopped, and the liquid surface of the acoustic matching member 800 is horizontal.

Position information of the supporting unit 400 is sent to the computer 700. When it is determined that the supporting unit 400 is in a position to start the measurement with the turning radius $r_0$ based on the position information, the arithmetic unit 710 outputs a control signal so that the light source 100 generates light. The light is guided by the optical system 200, and the object E is irradiated via the acoustic matching member 800 (step S802). Then, the light with which the object E is irradiated is absorbed within the object E and generates photoacoustic waves. With the plurality of acoustic wave receiving elements 300, photoacoustic waves generated within the object E and propagated within the acoustic matching member 800 are received and converted to electrical signals. The electrical signals output from the acoustic wave receiving elements 300 are sent to the computer 700, and the arithmetic unit 710 determines that an electrical signal is output from all of the acoustic wave receiving elements 300.

Subsequently, the operator of the object information acquiring apparatus makes an input with the inputting unit 1000 to accelerate the movement velocity in a step-wise manner, in order to move the supporting unit 400 in the circular path with the turning radius $r_0$ from the stopped state (step S803). The scanner 500 causes the movement velocity to accelerate in a step-wise manner from the stopped state to move the supporting unit 400 in the circular path with the turning radius $r_0$. When the movement velocity increases, the inertia force that acts on the acoustic matching member 800 increases, and therefore the tilt of the liquid surface increases. Through the state in FIG. 1B and FIG. 2B, transition is made in a step-wise manner up to the state shown in FIG. 1C and FIG. 2C where the object E and the acoustic wave receiving element 300 are not acoustically coupled.

When even one electrical signal output from the acoustic wave receiving elements 300 that is sent to the computer 700 becomes absent, the arithmetic unit 710 determines that electrical signals are not output from part of the acoustic wave receiving elements 300 (Yes in step S804). Then, the movement velocity immediately before the electrical signals have ceased to be output from part of the acoustic wave receiving elements 300 is stored in the storage unit 720 as a movement velocity $v_{max}$ (mm/sec) that results in $F_{max}$ described above. The arithmetic unit 710 may determine that acoustic coupling is not accomplished, also in the case where the value of the electrical signal is an aberrant value outside a predetermined range. It is advisable for the arithmetic unit 710 to monitor the electrical signal constantly or at sufficiently short predetermined intervals. Upon setting $v_{max}$ (mm/sec), a velocity with a certain extent of extra margin may be used instead of the velocity immediately before disruption of the electrical signal.

Subsequently, with the arithmetic unit 710, the movement velocity v (mm/sec) for satisfying the condition of formula (3) in the spiral path shown in formula (1) is calculated, and a pattern of moving the supporting unit 400 is created and stored in the storage unit 720 (step S805). In one example of the movement region shown in FIG. 5, the radius (curvature radius) of the spiral path decreases along with the movement from the point A to the point B. That is, since the curvature increases bit by bit, the movement velocity v (mm/sec) is controlled to decelerate from the velocity $v_{max}$ (mm/sec) as the scanning position approaches the center, in order to satisfy the condition of formula (3). That is, the computer 700 controls the scanner 500 to decelerate the velocity of moving the supporting unit 400, in the case where the curvature of the curved path increases. In the case where a scanning unit constantly monitors an output signal upon moving on the curved path and disruption of the signal has been detected, it is also preferable to control the movement velocity based on the velocity v (mm/sec) at the time.

The scanner 500 is controlled by the arithmetic unit 710 such that the supporting unit 400 is moved at the movement velocity $v_{max}$ (mm/sec) from the point A shown in FIG. 5 and then moved to the point B according to the movement pattern stored in the storage unit 720 (step S806).

During the movement from the point A to the point B shown in FIG. 5, position information of the supporting unit 400 is sent to the computer 700, and the arithmetic unit 710 outputs a control signal so that the light source 100 generates light. The light is guided by the optical system 200, and the object E is irradiated via the acoustic matching member 800. Then, the light with which the object E is irradiated is absorbed within the object E and generates photoacoustic waves. With the plurality of acoustic wave receiving elements 300, photoacoustic waves generated within the object E and propagated within the acoustic matching member 800 are received and converted to an electrical signal as a received signal. The electrical signal output from the acoustic wave receiving element 300 is sent to the computer 700 to be associated with the position information of the supporting unit 400 and saved as an electrical signal in the storage unit 720 by the arithmetic unit 710. The light irradiation by the light source 100 is performed at constant intervals (for example, 10 Hz) regardless of the movement velocity of the supporting unit.

The arithmetic unit 710 acquires object information by carrying out processing based on an image reconstruction algorithm with respect to the acquired received signal (step S807). As the algorithm, a time-domain or Fourier-domain back projection or the like that is used normally in a tomography technique can be used, for example. In the case where much time can be provided for reconstruction or in the case where the computing capability of the computer is high, an inverse problem analysis method with repetitive processing may be used.

In the embodiment described above, the operator of the object information acquiring apparatus inputs the turning radius $r_0$ and the movement velocity to accelerate in a step-wise manner with the inputting unit 1000, when the movement velocity $v_{max}$ (mm/sec) is acquired. However, such procedure may be stored in the storage unit 720 as a program and made performable by the object information acquiring apparatus.

Processing to obtain the velocity $v_{max}$ (mm/sec) may be performed before the acquisition of the actual object information. For example, it is suitable at a timing of shipment or installation of the apparatus, at a time of periodic inspection or correction, on a daily basis, on a subject basis, or the like.

Even in the case where the curved path is not spiral, $v_{max}$ (mm/sec) can be acquired with the same method as the above by causing the supporting unit to accelerate in a step-wise manner in the circular path with a radius on the outermost side of the curved path.

In this manner, in this embodiment, the supporting unit is controlled to decelerate in the case where the curvature of the curved path increases. Therefore, since inertia force satisfying the condition of formula (3) acts on the acoustic matching member with which the supporting unit is filled, acoustic coupling between the object E and the acoustic wave receiving element can be held. As a result, clear reception of acoustic waves is made possible in the apparatus in which the sensor holding the acoustic matching member is moved to receive acoustic waves from the object.

(Embodiment 2)

In Embodiment 1, the specific method for controlling the velocity of moving the supporting unit 400 to satisfy the condition of formula (3) has been described. In Embodiment 2, a method of controlling the velocity of moving the supporting unit 400 with a different method will be described.

In this embodiment, the object E shown in FIG. 1 and FIG. 2 is expected to be a breast, the shape holding unit 1100 is a holder in the shape of a partial sphere, and the supporting unit 400 is in a rotationally symmetrical shape about the central axis of a hemisphere. The movement of the supporting unit 400 in the X- and Y-directions is performed along the spiral path shown in FIG. 5, in a similar manner to Embodiment 1.

Figure 6:
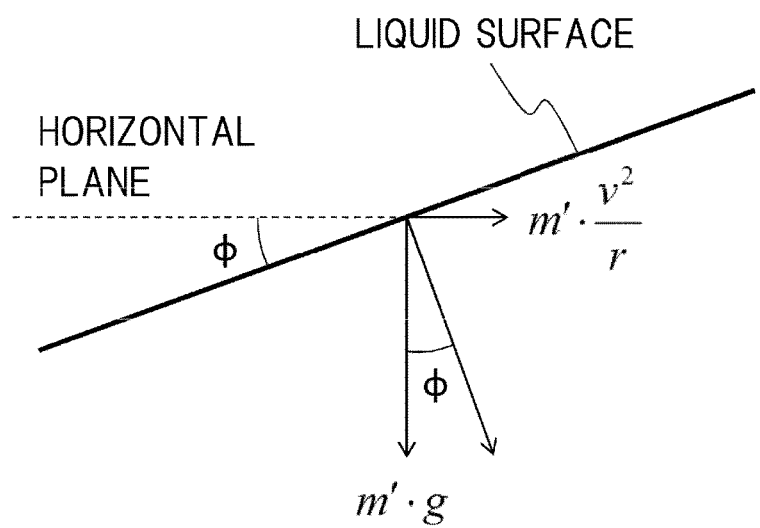
FIG. 6 is a diagram representing the tilt angle of the liquid surface of an acoustic matching member.

FIG. 6 represents a state where a certain amount of inertia force has acted on the acoustic matching member 800 with which the supporting unit 400 is filled and tilted the liquid surface. The turning radius in the spiral path is r, the movement velocity at the turning radius r is v, and the gravitational acceleration is g. To consider a micro mass m' of one portion of the acoustic matching member 800, gravity and inertia force act on the micro mass m', and the liquid surface is tilted by the resultant force. At this time, an angle φ by which the liquid surface of the acoustic matching member 800 is tilted with respect to the horizontal plane is represented by the following formula (4) from FIG. 6.

[Math. 4]

$$\phi = \tan^{-1}\left(\frac{v^2}{r \cdot g}\right) \quad (4)$$

When the supporting unit 400 is moved in the spiral path, the inertia force that acts on the acoustic matching member 800 acts in the normal direction of the spiral path. Therefore, the direction in which the inertia force acts changes in accordance with the movement of the supporting unit. Since the supporting unit 400 is in the rotationally symmetrical shape about the central axis of the hemisphere in this embodiment, the angle φ by which the liquid surface of the acoustic matching member 800 is tilted with respect to the horizontal plane can be held constant, even if the direction in which the inertia force acts changes. Therefore, the configuration is particularly suitable for an apparatus for testing an object in an approximately rotationally symmetrical shape, such as a breast.

As described with FIG. 1C and FIG. 2C, the angle by which the liquid surface is tilted with respect to the horizontal plane increases, when the inertia force that acts on the acoustic matching member 800 increases. As a result, space (air layer) not filled with the acoustic matching member 800 is formed between the acoustic wave receiving element 300 and the object E. The acoustic wave receiving element 300 in such a state is not acoustically coupled with the object E and therefore cannot receive photoacoustic waves.

Assume that the maximum tilt angle of the liquid surface of the acoustic matching member 800 with respect to the horizontal plane is $\phi_{max}$, in the case where the object E and the acoustic wave receiving element 300 are acoustically coupled. At this time, the gap between the object E and the acoustic wave receiving element 300 can be filled with the acoustic matching member 800 by controlling the movement velocity v (mm/sec) to satisfy the condition of formula (5). Accordingly, the object E and the acoustic wave receiving element 300 can be acoustically coupled.

[Math. 5]

$$\phi_{max} \geq \tan^{-1}\left(\frac{v^2}{r \cdot g}\right) \quad (5)$$

Next, a specific method for controlling the movement velocity v (mm/sec) will be described.

First, the object E is inserted to the shape holding unit 1100, and the acoustic matching member 800 fills the gap between the supporting unit 400 and the shape holding unit 1100 and the gap between the shape holding unit 1100 and the object E. Subsequently, the shape information acquiring unit 600 acquires shape information of the object E with the method described earlier, and the acquired shape information of the object E is sent to the computer 700 and stored in the storage unit 720.

With the arithmetic unit 710, $\phi_{max}$ is calculated from the shape information of the object E and the positional relationship with the supporting unit 400 that is moved along the spiral path of formula (1), and stored in the storage unit 720.

Subsequently, with the arithmetic unit 710, the velocity v (mm/sec) for satisfying the condition of formula (5) in the spiral path shown in formula (1) is calculated, and a pattern of moving the supporting unit 400 is created and stored in the storage unit 720. In one example of the movement region shown in FIG. 5, the radius of the spiral path decreases along with the movement from the point A to the point B. Therefore, the movement velocity v for satisfying the condition of formula (5) is controlled to decelerate. That is, the computer 700 controls the scanner 500 to decelerate the velocity of moving the supporting unit 400, in the case where the curvature of the curved path increases.

The scanner 500 is controlled by the arithmetic unit 710 such that the supporting unit 400 is moved from the point A to the point B shown in FIG. 5 according to the movement pattern stored in the storage unit 720.

Then, with a procedure and method similar to Embodiment 1, object information can be acquired.

As described above, in this embodiment, the velocity of moving the supporting unit is controlled to decelerate in the case where the curvature of the curved path increases. Therefore, since inertia force satisfying the condition of formula (5) acts on the acoustic matching member with which the supporting unit is filled, the object E and the acoustic wave receiving element can be acoustically coupled.

Modified Example

In Embodiments 1 and 2 described above, the supporting unit starts from the point A and reaches the point B in the spiral path shown in FIG. 5. That is, the curvature of the curved path gradually increases, and the supporting unit is controlled to decelerate accordingly. However, even in the case where the supporting unit starts from the point B and reaches the point A (in the case of moving from the inside toward the outside), the movement velocity of the supporting unit can be controlled to satisfy the conditions of formula (3) and formula (5). Since the radius of the spiral path increases along with the movement from the point B to the point A in this case, the movement velocity v (mm/sec) gradually becomes higher in a range satisfying the conditions of formula (3) and formula (5). In other words, the velocity of moving the supporting unit is controlled to accelerate in the case where the curvature of the curved path decreases. With such control, the speed of moving the supporting unit can be increased in a portion where the curvature of the curved path is small. As a result, the measurement time can be shortened maximally, while stabilizing the acoustic matching member and maintaining the accuracy of measurement.

Upon moving the supporting unit on the curved path, a spiral path represented by formula (1) is used in Embodiments 1 and 2. However, as the path, other spirals such as a logarithmic spiral are acceptable, and a spiral based on an ellipse is also acceptable.

Figure 7:
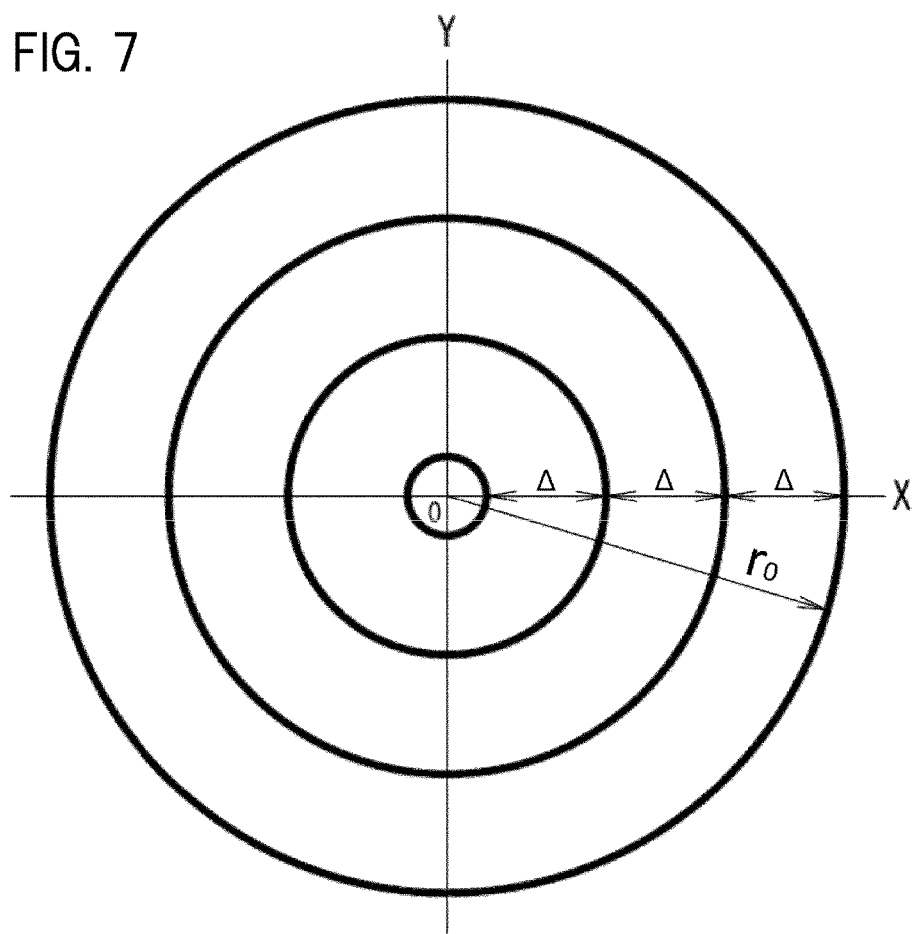
FIG. 7 is a diagram representing a modified example of the movement region of a supporting unit.

A combination of a plurality of circular motions of different radii as in FIG. 7 or a combination of a plurality of spiral motions is also acceptable. Specifically, concentric circles of different radii can be utilized as the path. Even with such paths, a method is applicable in which the supporting unit is gradually accelerated in the path on the outside, the velocity $v_{max}$ (mm/sec) immediately before detection of an output signal becomes absent is obtained, and the velocity is decreased toward the path on the inside.

As described above, the movement velocity of the supporting unit is controlled in accordance with the curvature of the curved path, at least in the case where the supporting unit is moved in the horizontal direction on the curved path formed of different curvatures (having portions of different curvatures). Accordingly, the gap between the object and the acoustic wave receiving element can be reliably filled with the acoustic matching member. Therefore, the two can be acoustically coupled. As a result, acoustic waves propagated from the object can be received clearly.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment (s) of the present invention, and by a method performed by the computer of the system or apparatus by, for example, reading out and executing the computer executable instructions from the storage medium to perform the functions of one or more of the above-described embodiment (s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An object information acquiring apparatus comprising:
a supporting unit configured to be capable of holding liquid acoustic matching member;
a plurality of receiving elements each supported on the supporting unit to receive an acoustic wave propagated from an object via the acoustic matching member and output an electrical signal;
a scanning unit that changes a relative position of the plurality of receiving elements and the object by moving the supporting unit;
a controlling unit that controls a velocity of movement of the supporting unit performed by the scanning unit; and
a processing unit that acquires specific information of an inside of the object based on the electrical signal,
wherein the scanning unit moves the supporting unit on a path having portions of different curvatures, and
the controlling unit controls the movement velocity in accordance with a magnitude of the curvature.

2. The object information acquiring apparatus according to claim 1, wherein the controlling unit decelerates the velocity of moving the supporting unit in a case where the curvature of the path increases.

3. The object information acquiring apparatus according to claim 1, wherein the controlling unit accelerates the velocity of moving the supporting unit in a case where the curvature of the path decreases.

4. The object information acquiring apparatus according to claim 1, wherein
the path is a spiral path,
the scanning unit moves the supporting unit from an outside toward an inside of the spiral path, and
the controlling unit decelerates the velocity of the supporting unit in accordance with the movement of the supporting unit.

5. The object information acquiring apparatus according to claim 1, wherein
the scanning unit moves the supporting unit in a circular path with a radius on an outermost side of the path,
the controlling unit accelerates the movement velocity of the supporting unit in a step-wise manner,
the processing unit detects whether values of electrical signals output by at least part of the receiving elements have fallen outside a predetermined range during the step-wise acceleration of the supporting unit, and
the controlling unit performs velocity control of the supporting unit based on the movement velocity of the supporting unit when the values of the electrical signals have fallen outside the predetermined range.

6. The object information acquiring apparatus according to claim 5, wherein, in a case in which the movement of the supporting unit causes an inertia force F to act on the acoustic matching member and tilt a liquid surface, and assuming the inertia force at maximum in a range in which the object and the receiving elements are acoustically coupled as $F_{max}$, a mass of the acoustic matching member on which the inertia force acts as m, the movement velocity of the supporting unit as v, and a radius of the path as r, the controlling unit controls the movement velocity v to satisfy a following formula:

[Math. 1]

$$F_{max} \geqq \frac{mv^2}{r}$$

7. The object information acquiring apparatus according to claim 5, further comprising an inputting unit with which an operator inputs the radius.

8. The object information acquiring apparatus according to claim 1, wherein the controlling unit controls the velocity of moving the supporting unit in a range that does not form an air layer between the object and the receiving elements.

9. The object information acquiring apparatus according to claim 1, wherein the supporting unit is in a spherical crown shape with the plurality of receiving elements arranged to form a high-sensitivity region in which receiving directions of the plurality of receiving elements converge.

10. The object information acquiring apparatus according to claim 1, wherein the acoustic matching member is water.

11. The object information acquiring apparatus according to claim 1, further comprising a shape holding unit to which the object is inserted to hold a shape of the object.

12. The object information acquiring apparatus according to claim 1, further comprising:
an optical system that irradiates the object with light,
wherein the acoustic wave is a photoacoustic wave propagated from the object irradiated with the light.

13. The object information acquiring apparatus according to claim 1, further comprising:
an acoustic wave transmitting unit that transmits an acoustic wave to the object,
wherein the receiving elements each receive a reflected wave reflected by the object after being transmitted from the acoustic wave transmitting unit.

14. An object information acquiring apparatus comprising:
a supporting unit configured to be capable of holding a liquid acoustic matching member;
a plurality of ultrasound wave receiving elements each supported on the supporting unit to receive an acoustic wave propagated from an object via the acoustic matching member;
a scanning unit that changes a relative position of the supporting unit and the object by moving the supporting unit; and
a controlling unit that controls a velocity of movement of the supporting unit performed by the scanning unit,
wherein the scanning unit moves the supporting unit on a path including a first portion having a first curvature radius and a second portion having a second curvature radius smaller than the first curvature radius, and
the controlling unit controls the movement velocity of the supporting unit such that the velocity of the supporting unit when moving in the second portion becomes lower than the velocity of the supporting unit when moving in the first portion.

15. The object information acquiring apparatus according to claim 14, wherein the supporting unit is approximately in a hemispherical shape.

16. The object information acquiring apparatus according to claim 14, wherein the path on which the supporting unit moves has a spiral shape.

* * * * *